United States Patent [19]
Joly et al.

[11] Patent Number: 5,444,175
[45] Date of Patent: Aug. 22, 1995

[54] PROCESS FOR THE ALKYLATION OF PARAFFINS

[75] Inventors: Jean-Francois Joly, Paris; Eric Benazzi, Montesson; Christian Marcilly, Houilles; Renaud Pontier, Vienne; Jean-Francois Le Page, Rueil Malmaison, all of France

[73] Assignee: Institut Francais Du Petrole, Rueil-Malmaison, France

[21] Appl. No.: 109,566

[22] Filed: Aug. 20, 1993

[30] Foreign Application Priority Data

Aug. 20, 1992 [FR] France .................... 92 10222
May 26, 1993 [FR] France .................... 93 06397

[51] Int. Cl.$^6$ .................... C07C 2/58; C07C 2/60; C07C 2/62
[52] U.S. Cl. .................... 585/714; 585/719; 585/731; 585/716; 585/722
[58] Field of Search .......... 585/714, 719, 731, 716, 585/722

[56] References Cited

U.S. PATENT DOCUMENTS

| | | | |
|---|---|---|---|
| 2,201,823 | 5/1940 | Bradley | 585/731 |
| 2,233,363 | 2/1941 | Frey et al. | 196/10 |
| 2,409,681 | 10/1946 | Hill et al. | 260/683.4 |
| 2,433,944 | 1/1948 | Draeger et al. | 260/683.4 |
| 3,371,127 | 2/1968 | Cabanaw et al. | 260/683.43 |
| 3,879,489 | 4/1975 | Yurchak et al. | 585/731 |

FOREIGN PATENT DOCUMENTS

| | | |
|---|---|---|
| 857145 | 8/1940 | France . |
| 1245853 | 10/1989 | Japan . |
| 1245854 | 10/1989 | Japan . |
| 540824 | 10/1941 | United Kingdom . |

*Primary Examiner*—Asok Pal
*Attorney, Agent, or Firm*—Millen, White, Zelano, & Branigan

[57] ABSTRACT

The invention relates to an alkylation process, in which a charge incorporating at least one isoparaffin and at least one olefin containing 2 to 6 carbon atoms per molecule, is treated in the presence of a solid alkylation catalyst. In the process, catalyst present in a reaction R is contacted with the charge, recycled liquid effluent discharged from reaction zone R and liquid effluent discharged from an isobutane/n-butane/alkylate separation zone S. The process uses a specific catalyst, e.g., sulfuric acid impregnated on a porous support.

20 Claims, 1 Drawing Sheet

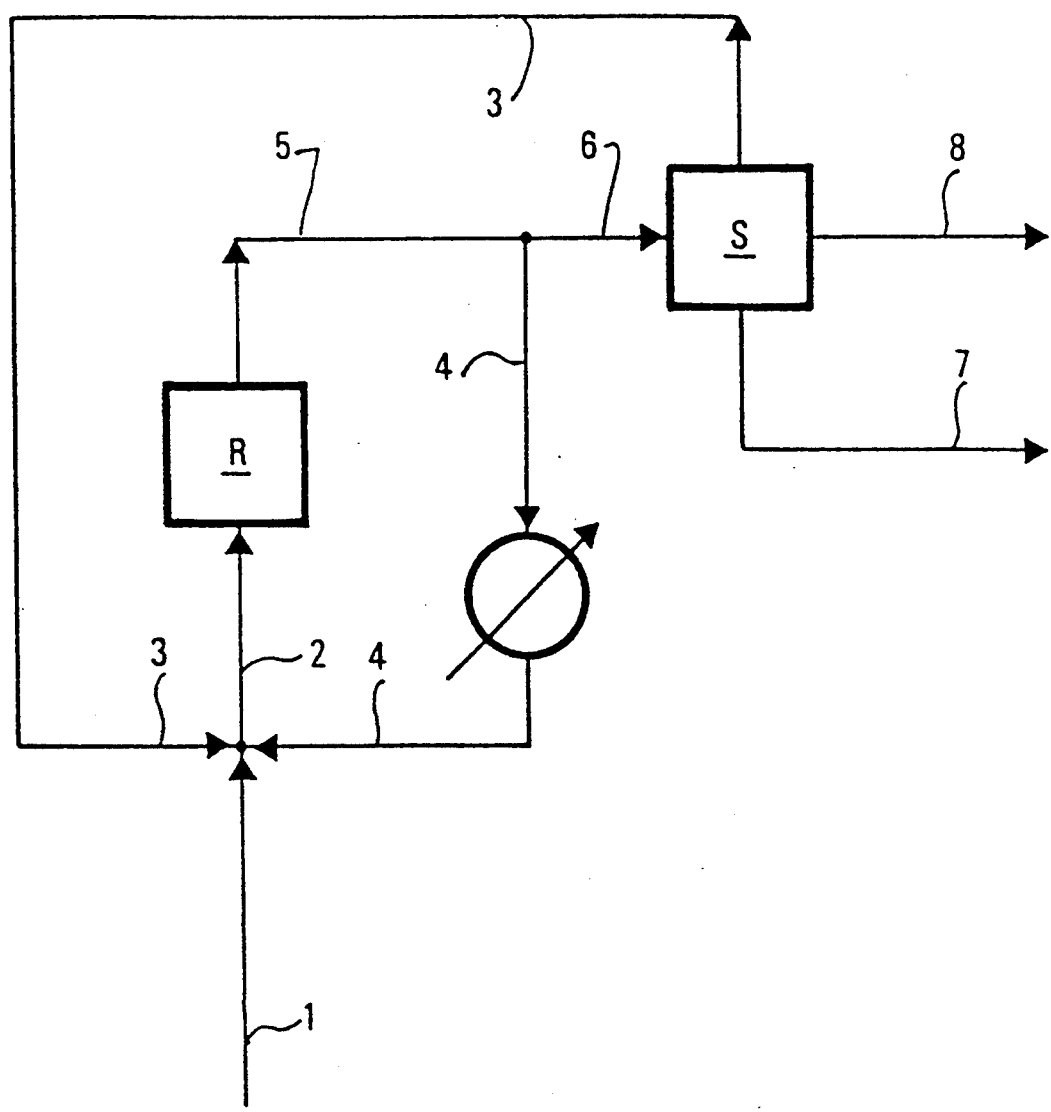

PROCESS FOR THE ALKYLATION OF PARAFFINS

SUMMARY OF THE INVENTION

The present invention relates to a novel process for the alkylation of at least one isoparaffin, preferably isobutane and/or isopentane, by at least one olefin containing 2 to 6 carbon atoms per molecule.

For the supply of controlled ignition internal combustion engines and in particular high compression ratio engines, it is of particular interest to have high-octane fuels, i.e., essentially comprising highly branched paraffinic hydrocarbons. The alkylation of isoparaffins (preferably isobutane and/or isopentane) by olefins containing 2 to 6 carbon atoms per molecule makes it possible to obtain such products. This reaction requires the use of very acid catalysts, with the particular aim of reducing secondary reactions such as olefin polymerization and dimerization reactions, which supply less branched hydrocarbons and unsaturated hydrocarbons, cracking reactions and disproportionation reactions.

Existing industrial processes for the production of hydrocarbons by the alkylation of isobutane by olefins use as the catalyst either sulphuric acid or hydrofluoric acid. In these processes, the acid catalyst constitutes a liquid phase, which is contacted with the liquid olefin-isoparaffin mixture in order to form an emulsion. These processes are expensive and cause serious problems with regards to polluting slops, as well as safety.

Other processes exist, which make use of heterogeneous acid catalysts such as molecular sieves, macroreticular resins optionally associated with boron trifluoride ($BF_3$) perfluorine resins, Lewis and/or Bronsted acids deposited on different inorganic supports, chlorinated aluminas, graphites intercalated by Lewis and/or Bronsted acids and anions deposited on oxide supports such as $ZrO_2/SO_4$. Two types of such processes exist, namely (i) the catalyst is suspended in a hydrocarbon phase by vigorous stirring within the reactor, i.e., the case of the perfectly stirred reactor and (ii) the catalyst is in a fixed bed in the reactor.

Among the type (i) processes, reference can be made to U.S. Pat. No. 3,879,489 and U.S. Pat. No. 3,855,343. This procedure has a major disadvantage. Thus, the catalyst can be rapidly destroyed by abrasion, which leads to the problem of eliminating fines. An improvement to the performance of the type (ii) process described in U.S. Pat. No. 3,852,371 proposes an injection of the isoparaffin-olefin charge at different levels into the catalyst bed, with partial recycling at said same levels, which would appear more complex to control. U.S. Pat. No. 3,852,371 and U.S. Pat. No. 5,073,665, which describe a preferred fixed bed performance procedure, describe the partial recycling of the effluent passing out of the reactor to the reactor intake. Thus, in the case of a performance having at least one fixed catalyst bed, U.S. Pat. No. 5,073,665 uses an olefin supply for each fixed catalyst bed.

The process according to the invention relates to an alkylation process, in which treatment takes place of a charge incorporating, on the one hand, at least one isoparaffin, preferably at least one element chosen from within the group formed by isobutane and isopentane and in even more preferred manner isobutane, and, on the other hand, at least one olefin containing 2 to 6 carbon atoms per molecule, in the presence of a solid alkylation catalyst, said process comprising:

a) the introduction and contacting with the catalyst present in a reaction zone R of the following compounds:

(i) said charge, preferably introduced at least at the intake of the zone R, (ii) part of the liquid effluent described in b), introduced at least at the intake of the zone R and preferably introduced totally at the intake of the zone R and (iii) part of the liquid effluent described in d), preferably introduced at least at the intake of the zone R, b) the recycling of part of the liquid effluent passing out of the reaction zone R to the intake of said zone R, c) the introduction of another part of the liquid effluent passing out of the reaction zone R into an isobutane/n-butane/alkylate separation zone S, d) the recycling of the major part of the isobutane-rich liquid effluent from the zone S into the reaction zone R, e) the obtaining of an alkylate, as product, from the zone S and f) the obtaining of n-butane as purge from the zone S.

The invention is characterized in that the catalyst present in the zone R is a solid catalyst chosen from among the following catalysts:

- a catalyst incorporating at least sulphuric acid impregnated on a mineral or organic porous support, such as the catalysts described in French patent applications 91/13,303, 91/14,154, 91/14,155 and 92/02,482,

- a catalyst incorporating the mixture containing, on the one hand, at least one halide of a compound chosen from within the group formed by aluminum and boron and, on the other hand, at least one quaternary ammonium halide and/or amine halohydrate, such, as e.g., the catalyst described in French patent application 92/00,802.

The preferred catalyst of the present invention comprises at least sulphuric acid impregnated on an organic or mineral porous support.

Preferably, and in particular in the case of the preferred performance procedure of the process according to the invention, where the reaction zone R functions in fluid bed form, the catalyst is mainly constituted by substantially spherical grams of diameter between 40 and 400 $\mu$m, preferably between 80 and 150 $\mu$m.

According to one performance procedure of the process according to the invention, it is possible to introduce the charge, i.e., the compound (i) described in a), at several points of the zone R. These different injection points for the compound (i) are distributed along the reaction zone and preferably one of these injection points is the intake of said zone. For the performance procedure of the reaction, said distribution most advantageously takes place in accordance with the operating conditions and compounds present in the zone R.

According to another performance procedure of the process according to the invention, which may or may not be independent of that described hereinbefore, it is possible to introduce the compound (ii) described in a) at several points of the zone R. These different injection points for the compound (ii) are distributed along the reaction zone, but one of the said injection points is always the intake of said zone. For the performance of the reaction, said distribution most advantageously takes place in accordance with the operating conditions and compounds present in the zone R.

According to another preferred performance procedure of the process according to the invention, which may or may not be independent of those described hereinbefore, it is possible to introduce the compound (iii) described in a) at several points of the zone R. These different injection points for the compound (iii) are distributed along the reaction zone and preferably one of these injection points is the intake of said zone. Most advantageously for the performance of the reaction, said distribution takes place in accordance with the operating procedures and compounds present in the zone R.

Preferably, the fractions of the compounds (i) to (iii) described in a) introduced into the zone R are partly or completely mixed and are preferably completely mixed before being introduced into said zone.

In another preferred performance procedure of the process according to the invention, the reaction zone functions as a fluid bed. In this case, the catalyst is fluidized by the mixture described in a). One of the advantages of this preferred procedure is that the speed of mixing in the reaction zone R governs the height of the catalyst bed. Other advantages of this procedure are the ease with which it is possible to draw off or add the catalyst with respect to said zone R, the possible elimination in the liquid by entrainment of grains of catalysts, which have lost matter by abrasion, and the obtaining of good stirring in the vicinity of the grains of catalysts, while limiting shocks between the individual grains.

The temperature in the reaction zone R is generally between $-30$ and $+5°$ C., preferably between $-15$ and $0°$ C., and the pressure is such that any product injected into the zone R, at whatever injection level, optionally incorporating a fraction of compound (i) and/or optionally a fraction of compound (ii) and/or optionally a fraction of compound (iii), is liquid on injection into the said zone. In preferred manner the elimination of calories takes place by a heat exchanger located on the recycling circuit (stage b, compound (ii)).

Preferably, the charge is dried on a molecular sieve and hydrogenated selectively prior to its introduction into the reaction zone R, so as to eliminate the very highly unsaturated compounds liable to inhibit the catalytic phase.

Generally, the molar ratio [sum of the (isobutane and/or isopentane) present in the compounds (i) and (iii) described in a) ]/[sum of the olefins present in the compounds (i) and (iii) described in a) ] is between 1 and 100, preferably between 3 and 50 and in even more preferred manner between 5 and 15.

The ratio of the mass flow of the compound (ii) and the sum of the mass flows of the compounds (i) and (iii) is generally between 2 and 10,000 and preferably between 5 and 1000.

In the case of the preferred performance procedure of the process according to the invention, where the reaction zone functions as a fluid bed, the velocity of the liquid phase in said zone is generally between 0.1 and 50 mm/s, as a function of the density of the grains and the diameter of the catalyst grains, so as to ensure fluidization. The reagents are introduced in such a way that the space velocity, expressed as weight of olefins introduced per weight unit of the catalyst and per hour, is generally between 0.001 and 10 $h^{-1}$ preferably between 0.0002 and 2 $h^{-1}$ and in even more preferred manner between 0.015 and 0.1 $h^{-1}$.

BRIEF DESCRIPTION OF THE DRAWINGS

FIG. 1 illustrates an embodiment of the invention and more specifically a performance procedure of the process according to the invention, without limiting the scope thereof.

DETAILED DESCRIPTION

The liquid phase mixture, incorporating at least one isoparaffin, preferably at least one element chosen from within the group formed by isobutane and isopentane, at least one olefin containing 2 to 6 carbon atoms per molecule, is introduced by the line (1) and then by the line (2) after mixing with the liquid effluents of the lines (3) and (4) in the reaction zone R.

A heat exchanger located on the line (4) makes it possible to eliminate the heat given off by the reaction and maintain the temperature of the liquid in the reactor at the desired value.

Part of the liquid effluent passing out from the zone R by the line (5) is recycled by the line (4) and then the line (2), after mixing with the liquid streams of the lines (1) and (3), to the reaction zone R. That part of the liquid effluent passing out of the reaction R and which is not recycled to the intake of said zone R, is supplied by the line (6) to an isobutane/n-butane/alkylate separation zone S. The alkylate separated in the zone S is extracted from the unit as product by the line (7). The n-butane is laterally extracted from the zone S by the line (8) as purge. The isobutane-rich liquid fraction extracted at the head of the zone S is recycled to the intake of the reaction zone R by the line (3).

EXAMPLES

The following example illustrates the invention without limiting its scope.

Example (i) Preparation of the catalyst

The catalyst is prepared by carrying out a dry impregnation of 54 g of a silica characterized by a total pore volume of 1.2 cm³/g, a specific surface equal to 55 m²/g, and which has been calcined in air at 150° C. for 12 hours by 48 cm³ of a solution containing 95% by weight of sulphuric acid of titre 98.7% and 5% by weight of trifluoromethane sulphonic acid of titre 98%. The thus obtained catalyst is kept protected from air to the time of use.

(ii) Catalytic test conditions for alkylating isobutane

To alkylate isobutane by 1-butene, use is made of a tubular reactor of internal diameter 4.2 cm and height 33 cm. This reactor, which contains 140 g of the catalyst prepared in (i), is supplied from the bottom by a liquid phase, whose linear velocity in the reactor is 1.2 cm/sec and which is adequate for ensuring the fluidization of the catalyst.

In order to simulate the recycling of the isobutane from the separation zone S to the intake of the reactor, the charge is constituted by a liquid mixture of isobutane and 1-butene containing 8.5% by weight of 1-butene. The injection volume flow rate of the charge described hereinbefore is 100 ml/h.

The major part of the liquid effluent passing out of the reactor is recycled to the intake of said reactor after mixing with the charge. For this purpose use is made of a recycling volume flow of 50 l/h. Continuous drawing off takes place from the unit at a flow rate close to 100 ml/h of a liquid phase containing isobutane, unconverted 1-butene and the alkylate produced. The alkylate is separated from said mixture by isobutane vaporization.

The temperature of the liquid phase in the reactor is $-5°$ C. To maintain a temperature of $-5°$ C., use is made of a heat exchanger constituted by a coil having a volume of 200 ml located on the recycling circuit and immersed in a bath cooled to $-12°$ C.

The weight composition of the alkylate collected after 200 continuous test hours is as follows:

$C_5$-$C_7$ 5.5%
$C_8$ : 92%
$C_9^+$ : 2.5%

The trimethyl pentane content in the $C_8$ fraction is equal to 91.5%. The 1-butene conversion is approximately 99.8%.

We claim:

1. An alkylation process wherein a charge containing at least one isoparaffin and at least one olefin containing 2 to 6 carbon atoms per molecule, is treated in the presence of a solid alkylation catalyst, said process comprising:
   a) introducing and contacting with catalyst present in a reaction zone:
      (i) said charge,
      (ii) recycled liquid effluent described in b), introduced at least at the intake of said reaction zone, and
      (iii) recycled liquid fraction described in d);
   b) recycling part of liquid effluent discharged from said reaction zone to the intake of reaction zone;
   c) introducing another part of said liquid effluent discharged from said reaction zone into an isobutane/n-butane/alkylate separation zone;
   d) recycling a part of an isobutane-rich liquid fraction from said separation zone to said reaction zone;
   e) recovering a product alkylate fraction from said separation zone; and
   f) recovering a n-butane fraction, as purge, from said separation zone;
   wherein said catalyst in said reaction zone is:
   a catalyst incorporating at least sulfuric acid impregnated on an organic or mineral porous support; or
   a catalyst incorporating a mixture containing at least one halide of a compound of aluminum or boron and at least one quaternary ammonium halide or an amine halohydrate, said mixture being impregnated on an organic or mineral porous support.

2. A process according to claim 1, wherein said at least one isoparaffin is isobutane or isopentane.

3. A process according to claim 1, wherein said charge is introduced into said reaction zone at several points, including intake of said reaction zone.

4. A process according to claim 1, wherein recycled isobutane-rich liquid is introduced into said reaction zone at several points, including the intake of said reaction zone.

5. A process according to claim 1, wherein said charge, recycled liquid effluent discharged from said reaction zone and recycled isobutane-rich liquid are introduced at the intake of said reaction zone, and are mixed together, totally or partly, before being introduced into said reaction zone.

6. A process according to claim 1, wherein recycled liquid effluent discharged from said reaction zone is totally introduced at the intake of said reaction zone.

7. A process according to claim 1, wherein said catalyst is predominantly substantially spherical grains having a diameter of 40–400 μm.

8. A process according to claim 1, wherein said reaction zone functions as a fluidized bed.

9. A process according to claim 1, wherein the ratio of mass flow rate of recycled liquid effluent discharged from said reaction zone and the sum of the mass flow rates of said charge and recycled isobutane-rich liquid is 2–10,000.

10. A process according to claim 1, wherein said catalyst comprises sulfuric acid impregnated on an organic or mineral porous support.

11. A process according to claim 1, wherein recycled liquid effluent discharged from said reaction zone is introduced into said reaction zone at several points, including the intake of said reaction zone.

12. A process according to claim 5, wherein said charge and said recycled isobutane-rich liquid are completely mixed before being introduced into said reaction zone.

13. A process according to claim 1, wherein, before introduction into the intake of said reaction zone, recycled liquid effluent discharged from said reaction zone is cooled by heat exchange.

14. A process according to claim 2, wherein the molar ratio of (a) the sum of isobutane and isopentane present in said charge and recycled isobutane-rich liquid to (b) the sum of olefin present in said charge and recycled isobutane-rich liquid is 1:100.

15. A process according to claim 1, wherein the space velocity within said reaction zone in terms of weight of olefins introduced per weight unit of catalyst per hour is 0.01–2 $h^{-1}$.

16. A process according to claim 1, wherein the space velocity within said reaction zone in terms of weight of olefins introduced per weight unit of catalyst per hour is 0.015–0.1 $h^{-1}$.

17. An alkylation process wherein a charge containing at least one isoparaffin and at least one olefin containing 2 to 6 carbon atoms per molecule, is treated in the presence of a solid alkylation catalyst, said process comprising:
   a) introducing and contacting with catalyst present in a reaction zone:
      (i) said charge,
      (ii) recycled liquid effluent described in b), introduced at least at the intake of said reaction zone, and
      (iii) recycled liquid fraction described in d);
   b) recycling part of liquid effluent discharged from said reaction zone to the intake of reaction zone;
   c) introducing another part of said liquid effluent discharged from said reaction zone into an isobutane/n-butane/alkylate separation zone;
   d) recycling a part of an isobutane-rich liquid fraction from said separation zone to said reaction zone;
   e) recovering a product alkylate fraction from said separation zone; and
   f) recovering a n-butane fraction, as purge, from said separation zone;
   wherein said catalyst is a mixture of an aluminum halide or a boron halide and either a quaternary ammonium halide or an amine halohydrate impregnated on an organic or mineral porous support.

18. A process according to claim 17, wherein said catalyst is a mixture of a boron halide and either a quaternary ammonium halide or an amine halohydrate impregnated on an organic or mineral porous support.

19. A process according to claim 10, wherein said catalyst is employed in said process directly after sulfur acid impregnation.

20. A process according to claim 10, wherein said catalyst, following sulfur acid impregnation, is protected from air and then used directly in said process.

* * * * *